United States Patent
Lancaster

(10) Patent No.: US 8,257,919 B2
(45) Date of Patent: Sep. 4, 2012

(54) MICRO-RNA PROFILES ASSOCIATED WITH ENDOMETRIAL CANCER DEVELOPMENT AND RESPONSE TO CISPLATIN AND DOXORUBICIN CHEMOTHERAPY

(75) Inventor: Johnathan M. Lancaster, Tampa, FL (US)

(73) Assignee: University of South Florida, Tampa, FL (US)

( * ) Notice: Subject to any disclaimer, the term of this patent is extended or adjusted under 35 U.S.C. 154(b) by 230 days.

(21) Appl. No.: 12/534,493

(22) Filed: Aug. 3, 2009

(65) Prior Publication Data

US 2009/0291452 A1 Nov. 26, 2009

Related U.S. Application Data

(63) Continuation of application No. PCT/US2008/055650, filed on Mar. 3, 2008.

(60) Provisional application No. 60/892,720, filed on Mar. 2, 2007.

(51) Int. Cl.
*C12Q 1/68* (2006.01)
(52) U.S. Cl. ............... 435/6; 435/325; 435/375; 514/44
(58) Field of Classification Search .................. None
See application file for complete search history.

(56) References Cited

U.S. PATENT DOCUMENTS

| 7,888,010 | B2 * | 2/2011 | Brown et al. | ................ | 435/6.14 |
| 2005/0176669 | A1 | 8/2005 | Al-Murrani | | |
| 2006/0078925 | A1 | 4/2006 | Mourelatos et al. | | |
| 2006/0189557 | A1 | 8/2006 | Slack et al. | | |
| 2009/0023149 | A1 * | 1/2009 | Knudsen | ........................... | 435/6 |

OTHER PUBLICATIONS

Roberts et al. (British Journal of Cancer 2005, vol. 92: 1149-1158).*
Gadducci et al. (Critical Reviews in Oncology/Hematology 2006: 242-256).*
Whitney et al. (Gynecologic Oncology 2004, (92): 4-9).*
Edmondson et al. (Journal of Tissue Culture Methods 1988).*

* cited by examiner

*Primary Examiner* — Kimberly Chong
(74) *Attorney, Agent, or Firm* — Michele L. Lawson; Smith & Hopen, P.A.

(57) ABSTRACT

A method predicting of cancer chemoresponse of the population of cancer cells to the one or more chemotherapeutic agents. Our ability to treat patients with advanced stage and recurrent endometrial cancer is hampered by an incomplete understanding of the molecular basis of disease development and response to therapy. A novel class of gene products called microRNA (miRNA) has recently been implicated in the etiology of several different human cancers. Altered levels of expression of specific miRNAs may contribute to cancer development in a variety of cancers such as endometrial cancer and may also influence response to cytotoxic chemotherapy or other cancer treatments. Evidence is provided that differential expression of miRNAs contributes to endometrial carcinogenesis and further associates with sensitivity of endometrial cancer cells to various chemotherapeutic agents including cisplatin and doxorubicin chemotherapy. MiRNA profiles and their gene targets show promise as biomarkers of endometrial cancer chemo-response, and as a novel class of therapeutic targets for patients with endometrial cancer.

13 Claims, 4 Drawing Sheets

MICRO-RNA PROFILES ASSOCIATED WITH ENDOMETRIAL CANCER DEVELOPMENT AND RESPONSE TO CISPLATIN AND DOXORUBICIN CHEMOTHERAPY

CROSS REFERENCE TO RELATED APPLICATIONS

This application is a continuation of prior filed International Application, Ser. No. PCT/US2008/055650 filed Mar. 3, 2008, which claims priority to U.S. Provisional Patent Application 60/892,720, filed Mar. 2, 2007, the contents of which are herein incorporated by reference.

FIELD OF INVENTION

This invention relates to cancer therapy. More specifically, this invention relates to micro-RNA profiles associated with endometrial cancer development and response to chemotherapeutic agents including cisplatin and doxorubicin.

BACKGROUND OF THE INVENTION

Cancer of the endometrium is the most common gynecologic malignancy and accounts for 6% of all cancers in women. It is estimated that there were over 39,000 new cases and approximately 7,400 deaths due to endometrial (uterine corpus) cancer in the United States in 2007. The cancer is considered a highly curable tumor. Endometrial cancer usually develops after menopause, between the ages of 50 and 60. Because it is usually associated with postmenopausal bleeding, this kind of cancer is often found at its earliest stage, when it is highly curable.

A number of factors have been found to increase a women's risk of developing endometrial cancer. One of the primary factors is unopposed estrogen replacement therapy/hormone therapy or tamoxifen therapy. There also appears to be genetic factors that increase the likelihood of disease, with the disease running in families.

Over 75% of endometrial cancers are adenocarcinomas. These form in the glandular cells located on the endometrium lining. Endometrioid adenocarcinomas are usually detected early and have a high rate of cure. About 10 percent of endometrial cancers are papillary serous adenocarcinomas, and 5 percent are clear cell adenocarcinomas. Both papillary serous adenocarcinomas and clear cell adenocarcinomas are more-aggressive types of endometrial cancer. They are more likely to recur or metastasize to another part of the body. Other types of endometrial cancer include adenosquamous carcinomas, which have elements of both adenocarcinoma and squamous cell carcinoma, and adenoacanthomas, in which squamous cells appear benign and glandular cells appear cancerous.

Four types of treatment for endometrial cancer have been proposed; surgery (including total hysterectomy, bilateral salpingo-oophorectomy, and radical hysterectomy), chemotherapy, radiation therapy, and hormone therapy. The choice of treatment is dictated by the stage of cancer.

MicroRNAs (miRNAs) are a new class of RNA's. Although they were first discovered in 1993, it has only been in the past few years that a more detailed understanding of their function and implications has begun to evolve. They are ~20-25 nucleotides in length. They function to regulate gene expression by inhibiting translation at the transcriptional and post-transcriptional level and degrading specific mRNAs. Growing evidence indicates that miRNAs are involved in proliferation, differentiation, apoptosis, growth, and development. They are further associated with control of oncogenes and tumor suppressor genes and are often found in fragile genomic regions involved in cancer. More than 200 miRNAs have been implicated in human carcinogenesis. Analysis of microRNA expression has shown that microRNA profiles could be of value in cancer diagnosis. A global downregulation of microRNA has been observed in tumors, and the microRNA profile also been shown to reflect the origin and differentiation state of the tumor.

Predicting the responsiveness of a tumor to a particular therapy has proven elusive. It would be highly advantageous to have refined methods of predicting the response to cancer treatment. For instance, in the case of chemotherapy, it would be highly desirable to be able to structure treatment regimens that allow a subject to avoid exposure to potentially toxic therapies that may derive little or no benefit to the patient in curing their condition. Similarly, methods of tailoring the optimal treatment regime could be effected where a timely and reliable system for predicting response is available to practitioners. The present invention solves this and other important needs in the art as will be apparent in the following.

SUMMARY OF INVENTION

Differential expression of miRNAs may contribute to carcinogenesis and further may influence sensitivity of cancer cells to various chemotherapeutic agents including cisplatin and doxorubicin chemotherapy. MiRNA profiles and their gene targets show promise as biomarkers of endometrial cancer chemo-response, and as a novel class of therapeutic targets for patients with endometrial cancer.

In a first aspect the present invention provides a method of predicting cancer chemoresponse of a population of cancer cells. The method includes the steps of assaying the miRNA profile of a sample from a population of cancer cells, comparing the miRNA profile of the assayed cells to profiles of miRNA from cancer cells with predetermined sensitivities to one or more chemotherapeutic agents and determining the predicted chemoresponse of the assayed cells to the one or more chemotherapeutic agents based upon the compared miRNA profiles. In certain embodiments the method includes the step of administering one or more chemotherapeutic agents to the population of cells responsive to the predicted chemoresponse of the assayed cells. The cancer associated with the population of cancer cells can be endometrial cancer. In certain embodiments the one or more chemotherapeutic agent can be doxorubicin, cisplatin, carboplatin, paclitaxel, cyclophosphamide, ifosfamide, methotrexate, vinblastine, etoposide, dactinomycin, topotecan or vinorelbine. The method can further include the step of administering hormonal therapeutic agents. Hormonal therapeutic agent can include megestrol, tamoxifen, medroxyprogesterone acetate, gonadotrophin-releasing hormone and lutenizing hormone-releasing hormone analogs, aromatase inhibitors, and LY353381.

In certain advantageous embodiments the miRNA is hsa-miR-193b, hsa-let-7i, hsa-miR-24, hsa-miR-181a, hsa-miR-320, hsa-miR-210, hsa-miR-200c, hsa-miR-106a, hsa-miR-221, hsa-miR520h, hsa-miR-320, hsa-miR-324-5b, hsa-miR-422b, hsa-miR-296, hsa-miR-let7a, hsa-miR-106a, hsa-miR-130b, hsa-miR-27a, or hsa-miR-23a. The chemoresponse of the population of cancer cells to one or more chemotherapeutic agents can be determined by MTT proliferation assays.

In a second aspect the present invention provides a method of predicting the cancer chemoresponse to cisplatin of the population of cancer cells. The method includes the steps of assaying the miRNA profile of a sample from a population of cancer cells, comparing the miRNA profile of the assayed cells to profiles of miRNA from cells with predetermined sensitivities to cisplatin and determining the predicted chemoresponse of the population of cancer cells to cisplatin based upon the compared miRNA profiles.

The method can further include the step of administering cisplatin to the population of cells responsive to the predicted chemoresponse of the population of cancer cells. In certain advantageous embodiments the miRNA is hsa-miR-let7a, hsa-miR-106a, hsa-miR-130b, hsa-miR-27a, or hsa-miR-23a. The cancer can be endometrial cancer.

In a third aspect the present invention provides a method of predicting the cancer chemoresponse to doxorubicin of the population of cancer cells. The method includes the steps of assaying the miRNA profile of a sample from a population of cancer cells, comparing the miRNA profile of the assayed cells to the miRNA profile of cells with predetermined sensitivities to doxorubicin and determining the predicted chemoresponse of the population of cancer cells to doxorubicin based upon the compared miRNA profiles of the cancer chemoresponse to doxorubicin of the population of cancer cells.

The method can further include the step of administering doxorubicin to the population of cells responsive to the predicted chemoresponse of the population of cancer cells.

In certain advantageous embodiments the miRNA is hsa-miR-193b, hsa-let-7i, hsa-miR-24, hsa-miR-181a, hsa-miR-320, hsa-miR-210, hsa-miR-200c, hsa-miR-106a, hsa-miR-221, hsa-miR520h, hsa-miR-320, hsa-miR-324-5b, hsa-miR-422b, or hsa-miR-296. The cancer can be endometrial cancer.

In a fourth aspect the present invention provides a method of generating biomarkers predictive of the responsiveness of a cancer to one or more chemotherapeutic agents. The method can include the steps of assaying miRNA expression in a population of cancer cells, correlating miRNA expression levels in the cancer cell population with the expression of miRNA in one or more control cell populations, determining the chemoresponse of the population of cancer cells to one or more chemotherapeutic agents and developing a profile correlating the relative miRNA expression level in the population of cancer cells to the cell's chemoresponse to the one or more chemotherapeutic agents. The step of correlating enables a determination of the overexpression or underexpression of the miRNA in the population of cancer cells. The chemoresponse of the population of cancer cells to one or more chemotherapeutic agents can be determined by MTT proliferation assays. The cancer can be endometrial cancer.

In a fifth aspect the present invention provides a method of predicting the treatment response of the population of cancer cells to the one or more cancer treatments. The method includes the steps of assaying the miRNA profile of a sample from a population of cancer cells, comparing the assayed miRNA profile of the assayed cells to profiles of miRNA from cancer cells with predetermined responsiveness to one or more cancer treatments and determining the predicted response of the population of cancer cells to the one or more cancer treatments based upon the compared miRNA profiles. The cancer treatment can be chemotherapy, radiation therapy, hormone therapy, surgery and combinations thereof.

The method can further include the step of the step of administering the one or more cancer treatments to the population of cells responsive to the predicted treatment response of the assayed cells.

In a sixth aspect the present invention provides a method of treating cancer in a subject including the step of targeting aberrantly expressed miRNA in the cancer cells of the subject in need of such treatment.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
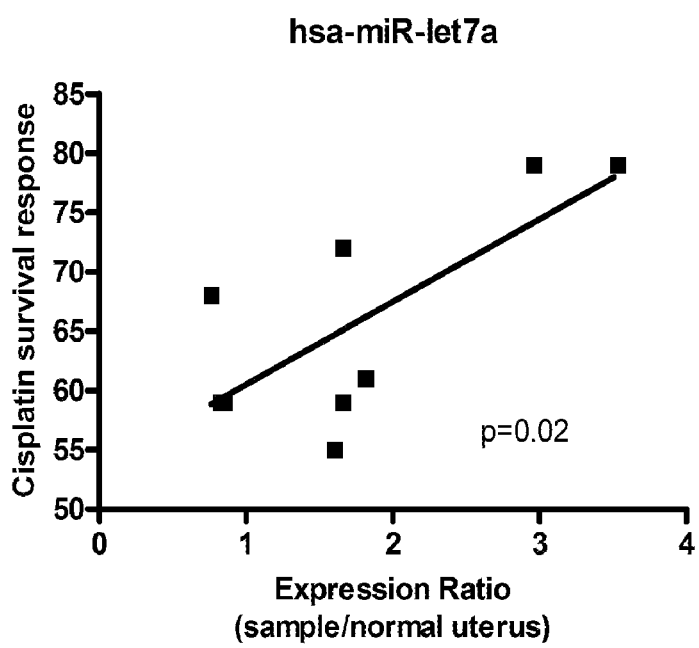
FIG. 1 is a graph showing the logistic regression analysis; endometrial cancer cell line response to cisplatin with respect to has-miR-let7a miRNA expression.
Figure 2:
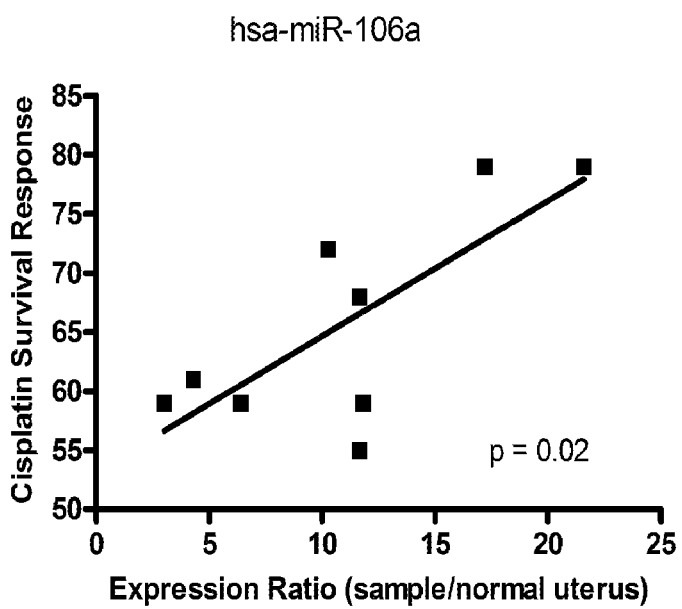
FIG. 2 is a graph showing the logistic regression analysis; endometrial cancer cell line response to cisplatin with respect to has-miR-106a miRNA expression.
Figure 3:
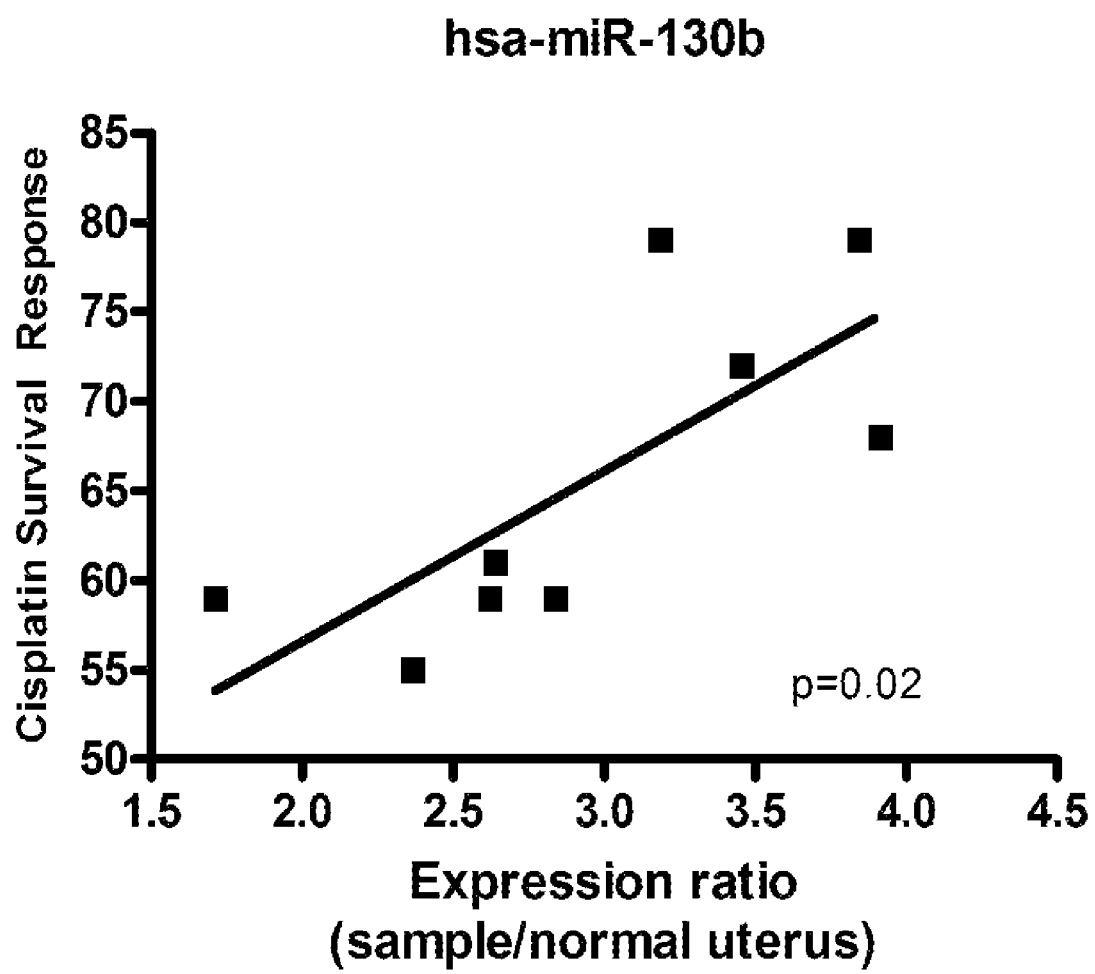
FIG. 3 is a graph showing the logistic regression analysis; endometrial cancer cell line response to cisplatin with respect to has-miR-130b miRNA expression.
Figure 4:
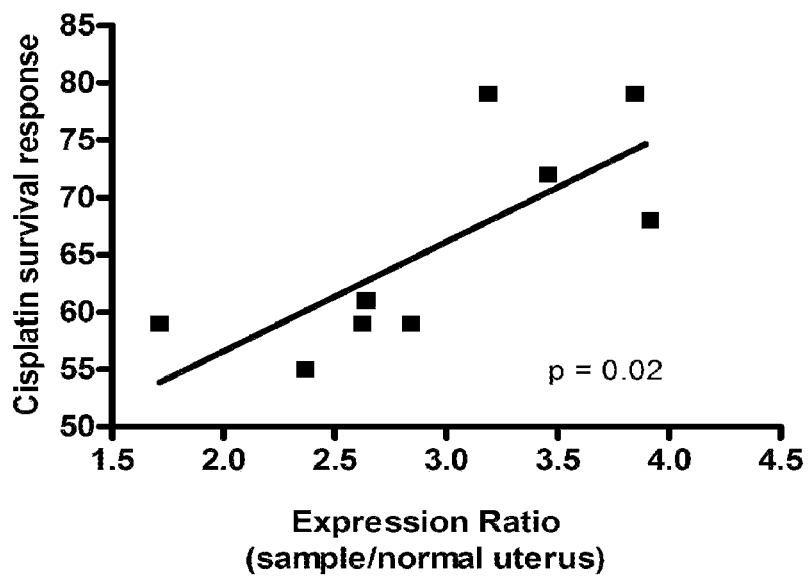
FIG. 4 is a graph showing the logistic regression analysis; endometrial cancer cell line response to cisplatin with respect to has-miR-23a miRNA expression.
Figure 5:
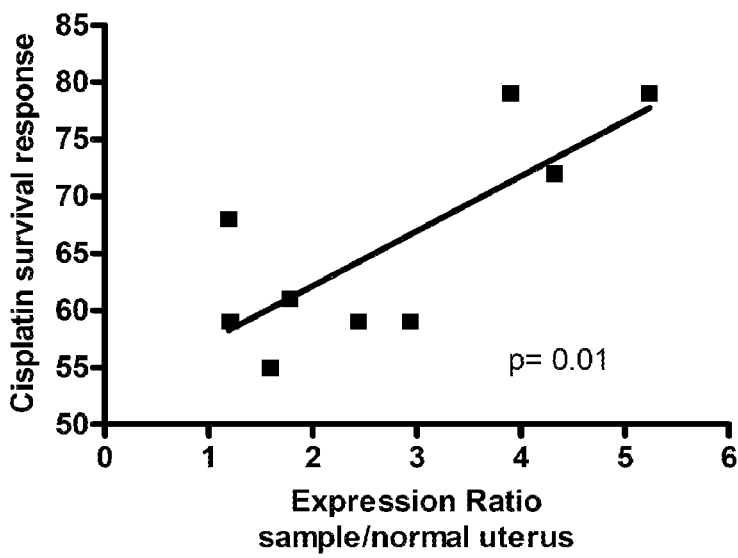
FIG. 5 is a graph showing the logistic regression analysis; endometrial cancer cell line response to cisplatin with respect to has-miR-27a miRNA expression.
Figure 6:
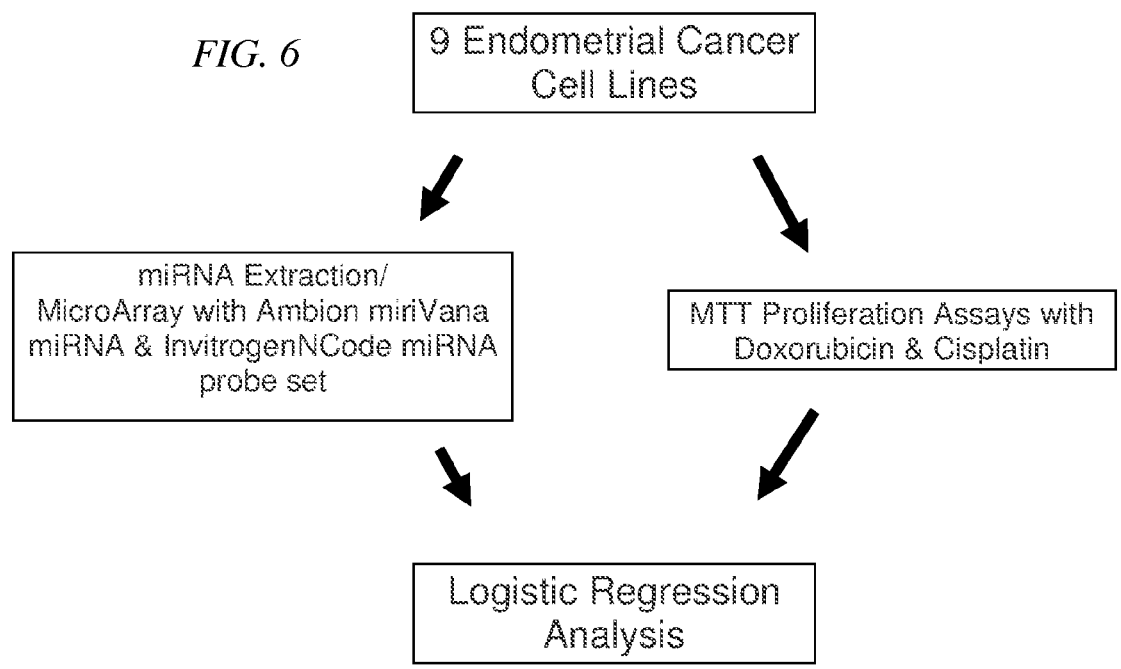
FIG. 6 is a flowchart showing an overview of the methodology.

Our ability to treat patients with advanced stage and recurrent endometrial cancer is hampered by an incomplete understanding of the molecular basis of disease development and response to therapy. A novel class of gene products called microRNA (miRNA) has recently been implicated in the etiology of several different human cancers. MicroRNAs are small non-coding nucleotide sequences that can bind messenger RNA to influence gene expression and protein translation. We postulated that altered levels of expression of specific miRNAs may contribute to endometrial cancer development and may also influence response to cytotoxic chemotherapy. This data provides evidence that differential expression of miRNAs may contribute to endometrial carcinogenesis and further may influence sensitivity of endometrial cancer cells to various chemotherapeutic agents including cisplatin and doxorubicin chemotherapy. MiRNA profiles and their gene targets show promise as biomarkers of endometrial cancer chemo-response, and as a novel class of therapeutic targets for patients with endometrial cancer.

Methods

Nine endometrial cancer cell lines were subject to culture followed by miRNA extraction. MicroRNA were labeled with the miRCURY LNA Array labeling kit. All samples were hybridized to a custom miRNA array that contained Ambion mirVana miRNA and the Invitrogen NCode miRNA probe sets, and compared to normal endometrium miRNA controls. Response of the endometrial cancer cell lines to cisplatin and doxorubicin was evaluated by MTT cell proliferation assays in triplicate. Logistic regression analysis was used to identify miRNAs associated with endometrial cancer cell lines and responsiveness to cisplatin and doxorubicin.

Results

Thirty-five miRNAs demonstrated 10-fold or higher expression in endometrial cancer cells compared to normal endometrial control miRNA, and 13 miRNAs demonstrated lower expression in endometrial cancer. Responsiveness of endometrial cancer cells to cisplatin correlated with expression of hsa-miR-let7a ($p=0.02$), hsa-miR-106a ($p=0.02$), hsa-miR-130b ($p=0.02$), hsa-miR-27a ($p=0.01$), and hsa-miR-23a ($p=0.02$). Doxorubicin responsiveness was associated with the expression of 16 miRNAs ($p<0.05$). Of interest, 23 genes, postulated to be targets of the 18 miRNAs, are represented in 80-gene predictors of doxorubicin response, previously reported by our group.

35 miRNAs demonstrated 10 fold or higher expression in endometrial cancer cell lines vs. normal endometrial control miRNA 13 miRNAs demonstrated lower expression in endometrial cancer cell lines 5 miRNAs were up-regulated in platinum-resistant endometrial cancer cell lines 14 miRNAs were identified to be associated with doxorubicin sensitivity

CONCLUSION

This data provides evidence that differential expression of miRNAs may contribute to endometrial carcinogenesis and further may influence sensitivity of endometrial cancer cells to various chemotherapeutic agents including cisplatin and doxorubicin chemotherapy. MiRNA profiles and their gene targets show promise as biomarkers of endometrial cancer chemo-response, and as a novel class of therapeutic targets for patients with endometrial cancer.

Table 1 presents genes implicated in doxorubicin (regular font) and cisplatin (bolded font) sensitivity that are also targets of miRNAs associated with chemo-response.

TABLE 1

| | |
|---|---|
| PKM2 | Pyruvate kinase, muscle |
| CASP1 | caspase 1, apoptosis-related cysteine peptidase (interleukin 1, beta, convertase) |
| CDKN1B | cyclin-dependent kinase inhibitor 1B(p27, Kip1) |
| CNOT4 | CCR4-NOT transcription complex, subunit 4 |
| COL6A3 | collagen, type VI, alpha 3 |
| DPP6 | dipeptidyl-peptidase 6 |
| PHF3 | PHD finger protein 3 |
| SKP1A | S-phase kinase-associated protein 1A(p19A) |
| CNNM2 | cyclin M2 |
| TAX1BP1 | Tax1 (human T-cell leukemia virus type I) binding protein 1 |
| ID1 | inhibitor of DNA binding 1, dominant negative helix-loop-helix protein |
| DGKZ | diacylglycerol kinase, zeta 104 kDa |
| KCTD2 | potassium channel tetramerisation domain containing 2 |
| UNC13B | unc-13 homolog B (*C. elegans*) |
| GORASP2 | golgi reassembly stacking protein 2, 55 kDa |
| MLANA | melan-A |
| PAK7 | p21 (CDKN1A)-activated kinase 7 |
| PMPCB | peptidase (mitochondrial processing) beta |
| PLP2 | proteolipid protein 2 (colonic epithelium-enriched) |
| WARS | tryptophanyl-tRNA synthetase |
| ANKRD10 | ankyrin repeat domain 10 |
| COASY | Coenzyme A synthase |
| GNAS | GNAS complex locus |
| HNRPU | heterogeneous nuclear ribonucleoprotein U (scaffold attachment factor A) |
| SETDB1 | SET domain, bifurcated 1 |
| DNAJC9 | DnaJ (Hsp40) homolog, subfamily C, member 9 |
| HSD17B1 | hydroxysteroid (17-beta) dehydrogenase 12 |
| LMNA | lamin A/C |
| NOLA3 | nucleolar protein family A, member 3 (H/ACA small nucleolar |
| TPR | translocated promoter region (to activated MET oncogene) |
| CNNM3 | cyclin M3 |
| LAPTM4B | lysosomal associated protein transmembrane 4 beta |
| PAM | peptidylglycine alpha-amidating monooxygenase |
| ZNP264 | zinc finger protein 264 |
| PSAP | prosaposin (variant Gaucher disease and variant metachromatic leukodystrophy) |
| IPO13 | importin 13 |

TABLE 2

MiRNAs associated with doxorubicin response.
Endometrial Cancer Cell Lines Dox

| | |
|---|---|
| *hsa-miR-193b* | *p = 0.01* |
| *hsa-let-7i* | *p = 0.03* |
| *hsa-miR-24* | *p = 0.04* |
| *hsa-miR-181a* | *p = 0.04* |
| *hsa-miR-320* | *p = 0.01* |
| hsa-miR-210 | p = 0.02 |
| *hsa-miR-200c* | *p = 0.03* |
| *hsa-miR-106a* | *p = 0.02* |
| hsa-miR-221 | p = 0.01 |
| *hsa-miR-520h* | *p = 0.007* |
| *hsa-miR-320* | *p = 0.01* |
| *hsa-miR-324-5b* | *p = 0.04* |
| *hsa-miR-422b* | *p = 0.04* |
| *hsa-miR-296* | *p < 0.05* |

Downregulated miRNA's - (bolded font)
Upregulated miRNA's - (italicized font)

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of predicting chemoresponse to a chemotherapeutic agent in endometrial cancer cells comprising the steps of;
    assaying the miRNA profile of a sample from a population of cancer cells (assayed cells);
    comparing the miRNA profile of the assayed cells to profiles of miRNA from cancer cells with predetermined sensitivities to one or more chemotherapeutic agents; and
    determining the predicted chemoresponse of the assayed cells to the one or more chemotherapeutic agents based upon the compared miRNA profiles, whereby differential expression of the miRNA of the assayed cells as compared to the cells that are sensitive to the chemotherapeutic agents indicates chemotherapeutic resistance.

2. The method according to claim 1 further comprising the step of administering one or more chemotherapeutic agents to the population of cells responsive to the predicted chemoresponse of the assayed cells.

3. The method according to claim 1 wherein the one or more chemotherapeutic agent is selected from the group consisting of doxorubicin, cisplatin, carboplatin, paclitaxel, cyclophosphamide, ifosfamide, methotrexate, vinblastine, etoposide, dactinomycin, topotecan and vinorelbine.

4. The method according to claim 2 further comprising the step of administering hormonal therapeutic agents.

5. The method according to claim 4 wherein the hormonal therapeutic agent is selected from the group consisting of megestrol, tamoxifen, medroxyprogesterone acetate, gonadotrophin-releasing hormone and lutenizing hormone-releasing hormone analogs, aromatase inhibitors, and LY353381.

6. The method according to claim 1 wherein the miRNA is an miRNA selected from the group consisting of hsa-miR-193b, hsa-let-7i, hsa-miR-24, hsa-miR-181a, hsa-miR-320, hsa-miR-210, hsa-miR-200c, hsa-miR-106a, hsa-miR-221, hsa-miR520h, hsa-miR-320, hsa-miR-324-5b, hsa-miR-422b, hsa-miR-296, hsa-miR-let7a, hsa-miR-106a, hsa-miR-130b, hsa-miR-27a, and hsa-miR-23a.

7. The method according to claim 1 wherein the chemoresponse of the population of cancer cells to one or more chemotherapeutic agents is determined by MTT proliferation assays.

8. A method of predicting the chemoresponse of endometrial cancer cells to cisplatin comprising the steps of;
   assaying the miRNA profile of a sample from a population of cancer cells (assayed cells);
   comparing the miRNA profile of the assayed cells to profiles of miRNA from cells with predetermined sensitivities to cisplatin; and
   determining the predicted chemoresponse of the population of cancer cells to cisplatin based upon the compared miRNA profiles, whereby upregulation of the miRNA of the assayed cells as compared to the cells that are sensitive to cisplatin indicates cisplatin resistance.

9. The method according to claim 8 wherein the miRNA is an miRNA selected from the group consisting of hsa-miR-let7a, hsa-miR-106a, hsa-miR-130b, hsa-miR-27a, and hsa-miR-23a.

10. The method according to claim 8 further comprising the step of administering cisplatin to the population of cells responsive to the predicted chemoresponse of the population of cancer cells.

11. A method of predicting chemoresponse to a chemotherapeutic agent in endometrial cancer cells comprising the steps of;
   assaying the miRNA profile of a sample from a population of cancer cells (assayed cells);
   comparing the miRNA profile of the assayed cells to the miRNA profile of cells with predetermined sensitivities to doxorubicin; and
   determining the predicted chemoresponse of the population of cancer cells to doxorubicin based upon the compared miRNA profiles, whereby differential expression of the miRNA of the assayed cells as compared to the cells that are sensitive to the chemotherapeutic agents indicates chemotherapeutic resistance.

12. The method according to claim 11 wherein the miRNA is an miRNA selected from the group consisting of hsa-miR-193b, hsa-let-7i, hsa-miR-24, hsa-miR-181a, hsa-miR-320, hsa-miR-210, hsa-miR-200c, hsa-miR-106a, hsa-miR-221, hsa-miR520h, hsa-miR-320, hsa-miR-324-5b, hsa-miR-422b, and hsa-miR-296.

13. The method according to claim 11 further comprising the step of administering doxorubicin to the population of cells responsive to the predicted chemoresponse of the population of cancer cells.

* * * * *